United States Patent [19]

Keggenhoff et al.

[11] Patent Number: 4,745,216
[45] Date of Patent: May 17, 1988

[54] PROCESS FOR THE PRODUCTION OF POLYISOCYANATES

[75] Inventors: Berthold Keggenhoff; Günther Ellendt; Marcel Petinaux, all of Krefeld; Alfred Mitschker, Odenthal; Peter M. Lange, Leverkusen, all of Fed. Rep. of Germany

[73] Assignee: Bayer Aktiengesellschaft, Leverkusen, Fed. Rep. of Germany

[21] Appl. No.: 715,716

[22] Filed: Mar. 25, 1985

[30] Foreign Application Priority Data

Apr. 7, 1984 [DE] Fed. Rep. of Germany ....... 3413174

[51] Int. Cl.⁴ .............................................. C07C 71/00
[52] U.S. Cl. ..................................... 560/347; 560/352
[58] Field of Search .................. 260/453 SP, 453 PH; 560/347, 352

[56] References Cited

U.S. PATENT DOCUMENTS 4,405,527 9/1983 Wegener et al. ..................... 260/453
4,507,464 3/1985 Rasshofer et al. .................. 528/288

FOREIGN PATENT DOCUMENTS 0071080 2/1983 European Pat. Off. ..... 260/453 PH
144559 10/1980 Fed. Rep. of Germany .
3306845 8/1984 Fed. Rep. of Germany .. 260/453 PH

OTHER PUBLICATIONS

Ullmanns Encyclopadie der Technischen Chemie, 4th Edition 1977, vol. 13, pp. 347 et seq.
Ullmanns Encyclopadie der Technischen Chemie, "Hormone bis Keramik", 4.
Auflage, Band 13, Verlag Chemie, Weinheim, N.Y., Seite 312 et seq.
Ullmanns Encyclopadie der Technischen Chemie, Band 13, Verlag Chemie, Weinheim, N.Y., Seite 295–299.

Primary Examiner—Alan Siegel
Attorney, Agent, or Firm—Gene Harsh; Joseph C. Gil; Lyndanne M. Whalen

[57] ABSTRACT

Polyisocyanates are produced by reacting a polyamide solution with a phosgene solution. After the product polyisocyanate has been recovered, the solvent or a portion of the solvent employed is treated with crosslinked polymers insoluble in the solvent which polymers contain primary and/or secondary alcoholic hydroxyl groups and/or primary and/or secondary amino groups. After treatment, the polymer and any reaction products are removed. The solvent may then be reused. Preferred solvents are chlorobenzene and o-dichlorobenzene. The preferred polymers are bead polymers or bead copolymers of (meth)acrylic acid or styrene/divinyl benzene copolymer.

18 Claims, No Drawings

PROCESS FOR THE PRODUCTION OF POLYISOCYANATES

BACKGROUND OF THE INVENTION

This invention relates to a process for the preparation of organic polyisocyanates in the presence of solvents in which the solvent is reused.

Organic polyisocyanates are produced on a large industrial scale by phosgenation of the corresponding primary polyamines in the presence of inert organic solvents such as chlorobenzene or orthodichlorobenzene (see e.g. Ullmanns Encyclopädie der technischen Chemie, 4th Edition (1977), Volume 13, pages 350 et seq).

In the preparation of the industrially important polyisocyanates, particularly in the preparation of hexamethylene diisocyanates, tolylene diisocyanates or polyisocyanates of the diphenyl methane series by phosgenation of the corresponding di-and polyamines, traces of byproducts containing isocyanate groups are invariably formed (e.g., 6-chloro-hexylisocyanate in the preparation of hexamethylene diisocyanate, tolyl isocyanate in the preparation of tolylene diisocyanates and phenyl isocyanate in the preparation of polyisocyanates of the diphenyl methane series by the phosgenation of aniline/formaldehyde condensates). Such unwanted isocyanate compounds seriously impair the quality of the desired end products (polyisocyanates). It has therefore been attempted to remove these impurities from the polyisocyanate by distillation together with the solvent after the phosgenation reaction and subsequently free the solvent from these impurities by an elaborate column distillation. The solvent can then be reused. This purification of the solvent by distillation requires considerable consumption of energy and expenditure in apparatus, and particular difficulties are encountered when the compounds have boiling points close to those of the solvents used.

German Offenlegungsschrifrt No. 3,129,270 describes a process for the preparation of polyisocyanates in the presence of solvents, in which the solvent is freed from traces of compounds containing isocyanate groups before it is reused. The solvent is treated with compounds containing isocyanate reactive hydrogen atoms, such as alcohols or amines, to convert the readily volatile isocyanates into reaction products containing urethane or urea groups. The treated solvent is then separated from these reaction products by distillation. Even though these reaction products (which have much higher boiling points than the isocyanate traces) are much more easily separated by distillation, removal of these by-products necessitates distillation of the whole quantity of solvent required for the preparation of the polyamine solution. This entails a high expenditure of energy due to the large quantity of solvent required.

If the ureas or urethanes formed in the process described in German Offenlegungsschrift No. 3,129,270 are not removed by distillation, they enter the phosgenation process when the solvent is subsequently reused and may undergo numerous further reactions with phosgene and with the newly formed isocyanates. The quality of the polyisocyanates and the yield of the diisocyanate which is to be distilled are thereby diminished.

SUMMARY OF THE INVENTION

It is therefore an object of the present invention to provide a new process for the removal of traces of isocyanate from the solvent leaving the process for the production of polyisocyanates, in which a solvent free from traces of isocyanate as well as other by-products could be obtained without distillation and reused in conventional industrial processes for the preparation of polyisocyanates.

It was surprisingly found that this problem of isocyanates and other by-products in the solvent to be reused could be solved by treating the solvent which was to be freed from traces of isocyanate with certain polymers and then separating the solvent mechanically from these polymers. The polymers employed are cross-linked polymers which are insoluble in the solvent and contain at least one functional group selected from primary alcoholic hydroxyl groups, secondary alcoholic hydroxyl groups, primary amino groups and secondary amino groups. It was particularly surprising to find that when these polymers were used as a solid phase, they were capable of binding the very low concentrations of isocyanates present if they were brought into contact with the solvent for a relatively short period. In fact, the polymers are capable of absorbing almost 50% of their own weight in isocyanates.

DETAILED DESCRIPTION OF THE INVENTION

The present invention relates to a process for the preparation of polyisocyanates by the reaction of solutions of polyamines from which the polyisocyanates are derived in an inert solvent with a solution of phosgene in an inert solvent by a single stage or multi-stage phosgenation reaction. After completion of the phosgenation reaction, the reaction mixture is distilled. The solvent is then treated to remove traces of isocyanate and reused for the preparation of amine solution and phosgene solution. In this process, the whole quantity of solvent recovered may be treated with compounds containing isocyanate reactive hydrogen atoms and subsequently freed from the reaction products formed by the reaction of these compounds containing isocyanate reactive hydrogen atoms with the isocyanate groups present in the solvent. It is also possible to treat only part of the solvent used for the preparation of amine solution by this method. The compounds containing isocyanate reactive hydrogen atoms used are cross-linked polymers which are insoluble in the solvent and contain primary or secondary alcoholic hydroxyl groups or primary or secondary aminic amino groups as functional groups. The solvent is separated from the reaction products and excess polymer by mechanical separation.

The principle employed in the process of the present invention for working up the solvent is particularly suitable for a multi-stage process for the preparation of polyisocyanates, composed of the following individual stages:

(a) reaction of (i) solutions of the polyamine(s) underlying the polyisocyanate(s) in an inert solvent with (ii) a solution of phosgene in an inert solvent in a single stage or multi-stage reaction of phosgenation;

(b) separation of the excess phosgene and of the hydrogen chloride formed from the liquid reaction mixture obtained by (a);

(c) separation of the solvent together with readily volatile compounds containing isocyanate groups from the solution obtained in (b) by evaporation and recovery of the product of the process as evaporation residue which is optionally subjected to a further process of distillation;

(d) recovery of a solvent containing volatile isocyanate compound(s) by condensation of the vapors obtained in (c) and reuse of part of the condensate for the preparation of amine solution (i) and of another part of the condensate for the preparation of phosgene solution (ii).

In one embodiment of this process, the total quantity of condensates obtained in (d) may be treated with compounds containing isocyanate reactive hydrogen atoms, optionally after the removal of residues of phosgene as head product by brief distillation but otherwise without any purification by distillation, and the treated condensate subsequently freed from the reaction products formed by the reaction of these compounds containing isocyanate reactive hydrogen atoms with the isocyanate-containing compounds present in the condensate.

In another embodiment of this process, that portion of solvent which is the condensate obtained in (d) which is to be used for preparation of the amine solution (i) is treated with compounds containing isocyanate reactive hydrogen atoms, optionally after removal of residues of phosgene as head product by brief distillation but otherwise without any purification by distillation, and the treated solvent is then freed from the reaction products of these compounds containing isocyanate reactive hydrogen atoms with the compounds containing isocyanate groups.

The phosgenation reaction is carried out in known manner, using solutions of polyamines in inert solvents and phosgene solutions in inert solvents. In the process of the present invention, this phosgenation reaction may be carried out either in one stage or in several stages. For example, phosgenation may be carried out by forming suspensions of carbamic acid chlorides at low temperatures and then converting these suspensions into polyisocyanate solutions at elevated temperatures ("cold/hot phosgenation"). Particularly suitable polyamine starting materials are the technically important polyamines such as hexamethylene diamine ; 2,4- and/or 2,6-diamino toluene; 2,4'- and 4,4'-diaminodiphenyl methane and their mixtures with higher homologues (known as "polyamine mixtures of the diphenyl methane series") which may be obtained in known manner by aniline/formaldehyde condensation ; 1,5-diaminonaphthalene ; 1-amino-3,3,5-trimethyl-5-aminomethyl-cyclohexane (isophorone diamine); tris-(isocyanatophenyl)-methane and perhydrogenated diaminodiphenyl methanes.

In the process of the present invention, the amine starting materials such as those mentioned as examples above may be used in the form of 3 to 40 wt. %, preferably 5 to 30 wt. % solutions in inert solvents. The phosgene required for the phosgenation reaction is generally used in the form of a 10 to 60 wt. %, preferably 25 to 50 wt. % solution in inert solvents.

Suitable inert solvents both for the polyamine and for phosgene are known to those in the art. Specific examples of appropriate solvents are chlorobenzene and dichlorobenzene.

After the phosgenation has been carried out by methods known in the art, the excess phosgene and the hydrogen chloride formed are removed by methods known in the art, such as by blowing them out with inert gas or by partial distillation. The phosgenation product present in the form of a solution is then separated, either simply by evaporation or by fractional distillation, into a gaseous phase containing volatile compounds with isocyanate groups and a liquid phase substantially made up of crude polyisocyanate. The liquid phase obtained may, if desired, be worked up by distillation in known manner if a pure polyisocyanate is to be produced. This separation of crude polyisocyanate and volatile compounds is generally carried out at a temperature of from 80° to 220° C. (preferably from 120° to 190° C.) at a pressure of from 10 to 4,000 mbar (preferably from 200 to 3,000 mbar).

The vapor containing volatile compounds with isocyanate groups is condensed to form a solvent condensate containing volatile isocyanates, in particular monoisocyanates. The quantity of isocyanate compounds present in the condensate (calculated as NCO with molecular weight 42) may amount to 50 to 5,000 ppm, in particular 100 to 1500 ppm (by weight).

The solvent is then reused for preparing a fresh batch of amine and phosgene solutions. In contrast to the known methods used in the art, however, subsequent purifications by distillation for removing compounds containing isocyanate groups (apart from brief distillation optionally carried out for removing residues of phosgene as head product) are replaced by one of the measures according to the present invention described below.

In the first embodiment of the process of the invention, the condensate containing isocyanate compounds is treated (before its separation into partial streams for the preparation of amine solutions (i) and phosgene solution (ii)), with a cross linked polymer which is insoluble in the solvent and contains at least one isocyanate reactive group selected from primary or secondary alcoholic hydroxyl groups or primary or secondary aminic amino groups particularly such groups which are attached to aliphatic carbon atoms. These polymers are used in the form of granulates or, preferably, in the form of beads. They may be either polycondensation resins or polymers or copolymers of (meth)acrylic acid derivatives or they may be styrene-divinylbenzene resins in which the isocyanate reactive groups were incorporated during their preparation or into which such reactive groups are introduced by known methods after their preparation.

These polymers generally have a structure corresponding to known ion exchange resins which are used, for example, for desalting water (see e.g. Ullmanns Encyclopädie der technischen Chemie, 4th Edition (1977), Volume 13, page 295 et seq). The methods for preparation of polymers as well as introduction of the above-mentioned functional groups therefore correspond to known methods for the preparation of ion exchange resins. For example, polycondensation resins based on aliphatic polyamines and epichlorohydrin which already contain secondary amino groups (from the process of preparation) are suitable for purposes of this invention. Bead copolymers containing hydroxyl groups may be prepared, for example, by the known method of styrene/divinyl benzene bead copolymerization using hydroxyalkyl acrylates or methacrylates. It is particularly preferred, however, to use styrene/divinyl benzene bead copolymers having a divinyl benzene content of at least 3 wt. % (preferably from 5 to 15 wt. %) into which primary or secondary (preferably primary) amino groups attached to aliphatic carbon atoms have been introduced after their preparation. Styrene/divinyl benzene bead copolymers in which amino methyl groups are incorporated, are particularly suitable. The introduction of amino methyl groups into such copolymers has been described in the above literature reference "Ullmann", on page 302. Secondary amino groups may be introduced into the copolymers, for example, by reaction of the corresponding chloromethylated intermediate products with primary amines. Bead polymers and copolymers of the above-mentioned type which have a macroporous structure are particularly preferred.

The quantity of isocyanate reactive groups contained in the polymers to be used is generally from 1 to 4, preferably from 2 to 3 gram equivalents/liter of the solvent-saturated polymer, which in many cases is swelled by the solvent. The average particle size of the solvent-free polymer used in the form of granulate or preferably in bead form is generally from 0.1 to 5 mm, preferably from 0.3 to 2 mm. The resins generally have a binding capacity of 100 to 400 g of isocyanate per liter of solvent saturated resin. 1 liter of resin is therefore capable of purifying up to 4 tonnes of a solvent having an isocyanate content of 100 ppm (by weight). From this data and consideration of the contact time, especially in the case of a continuous process, the quantity of resin required for a given quantity of solvent having a given level of impurities can be determined reliably by a short preliminary experiment.

The treatment of the condensate (obtained in the above described process step d) with the polymer required in the present invention may be carried out intermittently or, preferably, continuously, employing the technology developed for the treatment of water with ion exchange resins. The treatment may in particular be carried out in solid bed or fluidized bed reactors or in cascades of stirrer vessels. Fluidized bed reactors are preferred. The treatment may be carried out in one or more stages. It is generally carried out at temperatures in the range of 20° to 180° C., preferably 50° to 130° C. at normal pressure or an excess pressure of up to 5 bar.

Sufficient contact time with the polymer must be ensured and can easily be determined in preliminary experiments. Suitable contact times are dependent upon the treatment temperature. Contact times of 5 to 15 minutes, for example, have generally been found to be sufficient. During treatment, the polymer may take up about 20 to 50% of its own weight of isocyanate without its structure being destroyed.

After the treatment, the polymer should be mechanically separated (e.g. by decanting or filtration) by any one or more of the conventional methods used in ion exchange technology.

When the solvent has been freed from excess polymer and from the compounds containing isocyanate groups in the form of their reaction products with the polymer, it may be used again for the preparation of amine solution (i) and phosgene solution (ii). As a result, when all of the solvent-containing volatile isocyanate compounds are treated with crosslinked polymer in accordance with the process of this invention (first embodiment described above) polyisocyanates with a sharply reduced content of readily volatile isocyanate components are obtained. At the same time, the requirement in energy and apparatus for the work of distillation is very substantially reduced since no by-products are introduced into the polyisocyanates through the solvent.

Where only part of the solvent is to be treated with polymer (second embodiment) the solvent condensate (obtained in d) in the process (described in detail above) is divided into two partial streams according to the size of the stream of amine solution (i) and that of the phosgene solution (ii) and is reused as solvent for the preparation of these solutions. The proportions by weight of these solvent streams for the preparation of amine solution (i) and phosgene solution (ii) lies in the range of from 10:1 to 1:5 in both embodiments of the process of the present invention.

In the second embodiment of the process of the present invention, that partial stream of the solvent condensate which is to be used for the preparation of phosgene solution (ii) is reused untreated. Only the partial stream used for the preparation of amine solution (i) is subjected to treatment with the polymers. In accordance with a variant of this second embodiment, only a portion, amounting to at least 10 wt. %, preferably at least 50 wt. % of the partial stream used for the preparation of amine solution (i) is subjected to treatment with the polymer. This ensures that the total level of unwanted isocyanate compounds in the system does not exceed a tolerable maximum, since a portion of these isocyanate-containing compounds in the continuously circulated and returned solvent is continuously removed by the polymer.

The following examples serve to explain the process according to the present invention. All figures given in "ppm" refer to proportions by weight.

EXAMPLES

Example 1

30 ml of an anhydrous, macroporous styrene/divinyl benzene bead polymer (proportions by weight of styrene:divinyl benzene=11.5:1) which had swelled in chlorobenzene and contained 2.4 gram equivalents/liter of aminomethyl groups (based on the swelled polymer) were introduced into a 1 liter flask with stirrer. The average particle size of more than 80 wt. % of the polymer beads was in the range of 0.5 to 1.3 mm.

500 ml of chlorobenzene with a phenyl isocyanate content of 1030 ppm heated to 100° C. were added to the polymer. This solution corresponded to a solvent condensate obtained when the solvent was evaporated from the product of commercial phosgenation of aniline/formaldehyde condensates after removal of phosgene and hydrogen chloride and the evaporated solvent was subsequently condensed. The solution and bead polymer were stirred together for 10 minutes at 100° C. The stirrer was then stopped, whereupon the bead polymer rapidly settled, and the supernatant solvent was decanted off. This solvent had a phenyl isocyanate content of 20 ppm. Additional chlorobenzene with a phenyl isocyanate content of 1030 ppm was then similarly treated in 500 ml portions with the bead polymer left in the flask. A total of 7 portions (=3.5 l) were treated. The treated solvent had a phenyl isocyanate content of 20 ppm. When the 8th portion was treated, the phenyl isocyanate content after treatment was 40 ppm, in the 9th portion it was 170 ppm and in the 10th portion, 240 ppm. The experiment was then terminated. A total of 5 liters of chlorobenzene was thus purified with 30 ml of bead polymer, at which point the bead polymer had taken up 5.7 g of phenyl isocyanate. The bead structure of this resin was at this stage virtually unchanged. The treated chlorobenzene contained no by-products apart from the residues of phenyl isocyanate.

Example 2

50 ml of the bead polymer described in Example 1 were introduced into each stirrer flask of a 2-stage stirrer cascade. Wire screens were arranged at the overflow of each stirrer flask to retain the bead polymer in its flask. Each stirrer flask had a capacity for 250 ml of liquid up to the overflow.

Chlorobenzene containing 550 ppm of phenyl isocyanate was then introduced into the cascade at a temperature of 80° C. The output through the cascade was 2.5 liters per hour. The chlorobenzene discharged from the cascade initially had a phenyl isocyanate content of 20 ppm, which slowly increased to reach 100 ppm by the time 27 liters of chlorobenzene had passed through. The bead polymer in the first stage of the cascade was then removed while the bead polymer in the second stage was transferred to the first stage for further saturation and 50 ml of fresh bead polymer were introduced into the second stage. The same chlorobenzene solution was then treated again as described above, and after an output of 18 liters the phenyl isocyanate content in the discharge had risen from 20 ppm to 100 ppm.

From this experiment, the bead polymer was calculated to have the capacity to absorb 10.9 g of phenyl isocyanate for every 50 ml of bead polymer swelled with chlorobenzene or 218 g of phenyl isocyanate per liter of chlorobenzene-swelled polymer.

The treated chlorobenzene contained no by-products apart from residues of phenyl isocyanate. The bead structure of the resin remained virtually unchanged during the absorption of phenyl isocyanate.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the production of a polyisocyanate comprising
   (a) phosgenating a polyamine to form a polyisocyanate by reacting
       (1) a polyamine on which the polyisocyanate is based in solution in an inert solvent with
       (2) phosgene in solution in an inert solvent,
   (b) separating the solvent from the polyisocyanate,
   (c) treating the separated solvent to be reused in polyamine solution (1) with a cross-linked polymer which is insoluble in the solvent and which cross-linked polymer contains at least one functional group selected from the group consisting of primary alcoholic hydroxyl, secondary alcoholic hydroxyl, primary amino and secondary amino groups and
   (d) mechanically separating any excess cross-linked polymer and/or reaction product formed during treatment (c) from the treated solvent.

2. The process of claim 1 in which chlorobenzene or o-dichlorobenzene is the solvent treated in (c).

3. The process of claim 1 in which the cross-linked polymer is a polycondensation resin or polymer in granulated or bead form.

4. The process of claim 1 in which the cross-linked polymer is a bead polymer or bead copolymer of (meth)acrylic acid or styrene/divinyl benzene copolymer.

5. The process of claim 1 in which the cross-linked polymer is a macroporous styrene/divinyl benzene bead polymer having a primary and/or secondary amino group attached to an aliphatic carbon atom.

6. The process of claim 1 in which at least 10 wt. % of the solvent separated in step (b) is treated according to step (c).

7. A process for the production of a polyisocyanate comprising
   (a) phosgenating a polyamine to form a polyisocyanate by reacting
       (1) the polyamine on which the polyisocyanate is based in solution in an inert solvent with
       (2) phosgene in solution in an inert solvent,
   (b) separating any excess phosgene and any hydrogen chloride formed during the reaction of (a) from the reaction mixture,
   (c) separating the solvent and any highly volatile compounds containing isocyanate groups from the reaction mixture remaining after step (b) by evaporation,
   (d) recovering the product polyisocyanate which is the residue remaining after the evaporation of step (c),
   (e) recovering the solvent separated in step (c) by condensation of the vapors produced in step (c),
   (f) treating at least a portion of the solvent recovered in step (e) with a compound containing isocyanate-reactive hydrogen which compound is a cross-linked polymer that is insoluble in the solvent and contains at least one functional group selected from primary alcoholic groups, secondary alcoholic groups, primary amino groups and secondary amino groups and
   (g) removing by mechanical means any excess polymer or reaction product from the solvent treated in (f) to obtain reusable solvent.

8. The process of claim 7 in which the product polyisocyanate recovered in step (d) is further purified by distillation.

9. The process of claim 7 in which all of the solvent recovered in step (e) is subjected to the treatment of step (f).

10. The process of claim 7 in which the condensation product of step (e) is briefly distilled to remove any phosgene residue before being treated in accordance with step (f).

11. The process of claim 7 in which a portion of the condensation product of step (e) is treated in accordance with step (f).

12. The process of claim 11 in which the solvent obtained in step (g) is reused to produce amine solution to be phosgenated.

13. The process of claim 7 in which the solvent obtained in step (g) is reused to produce amine solution to be phosgenated.

14. The process of claim 7 in which the solvent treated in (f) is chlorobenzene or o-dichlorobenzene.

15. The process of claim 7 in which the cross-linked polymer is a polycondensation resin or polymer in granulated form.

16. The process of claim 7 in which the crosslinked polymer is a bead polymer or bead copolymer of (meth)acrylic acid or styrene/divinyl benzene copolymer.

17. The process of claim 7 in which the crosslinked polymer is a macroporous styrene/divinyl benzene bead polymer having a primary and/or secondary amino group attached to an aliphatic carbon atom.

18. The process of claim 7 in which at least 10 wt. % of the solvent separated in step (c) is treated in accordance with step (f).

* * * * *